United States Patent [19]
Tjon-Joe-Pin et al.

[11] Patent Number: 6,110,875
[45] Date of Patent: Aug. 29, 2000

[54] METHODS AND MATERIALS FOR DEGRADING XANTHAN

[75] Inventors: Robert M. Tjon-Joe-Pin; Michelle Alana Carr, both of Houston; Bing Yang, Spring, all of Tex.

[73] Assignee: BJ Services Company

[21] Appl. No.: 08/813,064

[22] Filed: Mar. 7, 1997

[51] Int. Cl.[7] .............................. C09K 7/02; C12P 39/00; E21B 43/22

[52] U.S. Cl. .......................... 507/201; 507/101; 507/921; 435/42; 435/104; 166/246; 166/300; 166/308

[58] Field of Search .................................. 507/921, 101, 507/201; 435/42, 104; 166/246, 300, 308

[56] References Cited

U.S. PATENT DOCUMENTS

| | | | |
|---|---|---|---|
| 2,602,778 | 7/1952 | Snyder et al. | 252/8.55 |
| 2,681,704 | 6/1954 | Menaul | 166/22 |
| 2,801,218 | 7/1957 | Menaul | 252/8.55 |
| 3,044,550 | 7/1962 | Eilers | 166/42 |
| 3,684,710 | 8/1972 | Cayle et al. | 252/8.55 R |
| 4,119,546 | 10/1978 | Wernau | 507/110 |
| 4,157,116 | 6/1979 | Coulter | 166/280 |
| 4,160,483 | 7/1979 | Thomas et al. | 166/307 |
| 4,342,866 | 8/1982 | Kang et al. | 536/119 |
| 4,343,363 | 8/1982 | Norton et al. | 166/281 |
| 4,410,625 | 10/1983 | Cadmus | 435/42 |
| 4,479,543 | 10/1984 | Kalfayan et al. | 166/300 |
| 4,502,967 | 3/1985 | Conway | 252/8.55 R |
| 4,514,309 | 4/1985 | Wadhwa | 252/8.55 R |
| 4,609,475 | 9/1986 | Hanlon et al. | 252/8.55 B |

(List continued on next page.)

FOREIGN PATENT DOCUMENTS

| | | |
|---|---|---|
| 0030393B1 | 6/1983 | European Pat. Off. . |
| WO 91/18974 | 12/1991 | WIPO . |
| WO94/01654 | 1/1994 | WIPO . |

OTHER PUBLICATIONS

Cadmus et al., "High–Temperature, Salt–Tolerant Xanthanase," *Journal of Industrial Microbiology*, 4:127–133, 1993.

Cadmus et al., "Biodegradation of Xanthan Gum by *Bacillus sp.*," *Applied and Environmental Microbiology*, 5–11, 1982.

Ahlgren, "Characterization of Xanthan Gum Degrading Enzymes from a Heat–stable, Salt–tolerant Bacterial Consortium," in *Microbial Enhancement of Oil Recovery: Recent Advances*, edited by Premuzic and Woodhead; published by Elsevier: Amsterdam, pp.55–63, 1993.

Ahlgren, "Enzymatic Hydrolysis of Xanthan Gum at Elevated Temperatures and Salt Concentrations," in *Gas, Oil and Environmental Biotechnology VI*, edited by Srivastava et al., published by Institute of Gas Technology: Des Plaines, pp.245–253, 1995.

Ahlgren, "Purification and Characterization of a Pyruvated–Mannose–Specific Xanthan Lyase from Heat–Stable, Salt–Tolerant Bacteria," *Applied and Environmental Microbiology*, 57(9):2523–2528, Sep. 1991.

(List continued on next page.)

*Primary Examiner*—Philip Tucker
*Attorney, Agent, or Firm*—Arnold, White & Durkee

[57] ABSTRACT

Xanthan molecules are degraded using an xanthanase enzyme complex that is stable at temperatures above 250° F., such as those temperatures found in some wellbores and process streams. The xanthanase enzyme complex is produced by a novel soil bacterium. The xanthanase enzyme complex may be used to remove xanthan based formation damage, such as drilling filter-cakes and filtrates, or to remove xanthan based filter-cakes and/or residues present in processing equipment. The xanthanase enzyme complex may also be used to reduce the viscosity of xanthan-containing fluids, such as hydraulic fracturing fluids, blocking gels, drilling muds, and process fluids. The xanthanase enzyme complex may also be used in conjunction with other well or process treatments, such as stimulations and cementing operations, to improve the effectiveness of these treatments.

38 Claims, 3 Drawing Sheets

U.S. PATENT DOCUMENTS

| | | | |
|---|---|---|---|
| 4,665,985 | 5/1987 | Berrod et al. | 166/281 |
| 4,690,891 | 9/1987 | Hou et al. | 435/42 |
| 4,713,449 | 12/1987 | Vanderslice et al. | 536/123 |
| 4,809,783 | 3/1989 | Hollenbeck et al. | 166/307 |
| 4,886,746 | 12/1989 | Cadmus et al. | 435/42 |
| 4,928,763 | 5/1990 | Falk | 166/250 |
| 4,996,153 | 2/1991 | Cadmus et al. | 435/209 |
| 5,032,297 | 7/1991 | Williamson et al. | 252/8.551 |
| 5,067,566 | 11/1991 | Dawson | 166/308 |
| 5,103,905 | 4/1992 | Brannon et al. | 166/250 |
| 5,126,051 | 6/1992 | Shell et al. | 210/632 |
| 5,165,477 | 11/1992 | Shell et al. | 166/291 |
| 5,201,370 | 4/1993 | Tjon-Joe-Pin | 166/300 |
| 5,224,544 | 7/1993 | Tjon-Joe-Pin et al. | 166/295 |
| 5,226,479 | 7/1993 | Gupta et al. | 166/300 |
| 5,247,995 | 9/1993 | Tjon-Joe-Pin et al. | 166/312 |
| 5,421,412 | 6/1995 | Kelly et al. | 166/300 |
| 5,441,109 | 8/1995 | Gupta et al. | 166/300 |
| 5,447,197 | 9/1995 | Rae et al. | 166/293 |
| 5,562,160 | 10/1996 | Brannon et al. | 166/250.1 |
| 5,566,759 | 10/1996 | Tjon-Joe-Pin et al. | 166/300 |

OTHER PUBLICATIONS

Ahlgren, "Purification and Properties of a Xanthan Depolymerase from a Heat–Stable Salt–Tolerant Bacterial Consortium," *Journal of Industrial Microbiology*, 12:87–92, 1993.

PCT Search Report dated Jun. 15, 1998.

Beall et al., "Evaluation of a New Technique for Removing Horizontal Wellbore Damage Attributable to Drill–in Filter Cake," *SPE 36429*, Oct. 6–9, 1996.

Borman, "Bacteria That Flourish Above 100° C. Could Benefit Industrial Processing," *C&EN–Science/Technology*, 31–34, Nov. 4, 1991.

Brannon and Tjon–Joe–Pin, "Application of Polymeric Damage Removal Treatment Results in Multi–Fold Well Productivity Improvement: A Case Study," *SPE 29822*, 491–501, Mar. 11–14, 1995.

Brannon and Tjon–Joe–Pin, "Biotechnological Breakthrough Improves Performance of Moderate to High–Temperature Fracturing Applications," *SPE 28513*, 515–530, Sep. 25–28, 1994.

Burnett, "Using a Physical Wellbore Model to Study Formation Damage Problems in Well Completions," *SPE 27393*, 495–504, Feb. 7–10, 1994.

Cadmus and Slodki, "Bacterial Degradation of Xanthan Gum," *Industrial Polysaccharides: Genetic Engineering, Structure/Property Relations and Applications* edited by M. Yalpani, 101–107, 1987.

Cadmus and Slodki, "Enzymic Breakage of Xanthan Gum Solution Viscosity in the Presence of Salts," *Developments in Industrial Microbiology*, 26:281–289, Aug. 11–17, 1984.

Hodge et al., "Evaluation and Selection of Drill–in Fluid Candidates to Minimize Formation Damage," *SPE 31082*, 101–115, Feb. 14–15, 1996.

Jeanes, "Applications of Extracellular Microbial Polysaccharide–Polyelectrolytes: Review of Literature, Including Patents," *J. Polymer Sci.: Symposium No. 45*, 209–227, 1974.

Kelly and Brown, "Enzymes From High–Temperature Microorganisms," *Current Opinion in Biotechnology*, 4:188–192, 1993.

LeBlanc, "Limiting, Treating Formation Damage in Horizontal, Extended Reach Wells," *Offshore*, 56–61, Jun. 1996.

McLarty et al., "Overview of Offshore Horizontal Drilling/Completion Projects in Unconsolidated Sandstones in the Gulf of Mexico," *OTC 7352*, 861–868, May 3–6, 1993.

Ryan et al., "Mud Clean–Up in Horizontal Wells: A Major Joint Industry Study," *SPE 30528*, 801–810, Oct. 22–25, 1995.

Slodki and Cadmus, "Production and Stability of Xanthan Gums; Xanthanases and Their Applicability," *Microbes and Oil Recovery vol. 1, International Bioresources Journal*, 190–199, 1985.

METHODS AND MATERIALS FOR DEGRADING XANTHAN

BACKGROUND OF THE INVENTION

1. Field of the Invention

This invention relates generally to degradation of xanthan molecules and, more specifically to degradation of xanthan molecules at moderate to high temperatures. In particular, this invention relates to a method for treating wells, subterranean formations, and other applications using a microbial xanthanase which is active at high temperatures and/or downhole conditions. This invention also relates to a soil bacterium capable of producing the microbial xanthanase.

2. Description of the Related Art

Polysaccharides represent one typical type of polymer used in drilling, completion, and remedial operations. Among other things, polysaccharides may be used as a part of fracturing gels for hydraulic fracturing, to thicken drilling fluids, to control fluid loss, and as a part of gravel packing and frac pack fluids. Polysaccharides may also be used in sand control fluids, blocking gels, and completion fluids. Filter-cakes, filtrate invasion, and other similar types of formation damage are phenomena which often occur during various procedures performed within a wellbore using polysaccharide polymers including, but not limited to, drilling, completion, workover, and stimulation procedures.

For example, during drilling operations polysaccharide-based fluids containing high concentrations of clays, such as bentonite, which are typically used for lubrication and cuttings transport. These fluids are known to cause damage to the permeability of the near wellbore area due to leakoff and mud cake or filter-cake deposition on the face of production zones. A filter-cake is typically a dense and nearly water insoluble residue that may, among other things, serve to reduce the permeability of a subterranean formation. Filter-cakes may be formed when gel fluids leak into a formation matrix through rock pore spaces. In this case, the pores of a formation act as filters which permit fluid to leak into the matrix while filtering out the gel. This causes a layer of filtered gel to deposit on the face of the matrix, plugging the formation. In other cases, incomplete gel degradation may also result in the formation of a polysaccharide filter-cake. A filter-cake may contain precipitates, such as silicates from drilling muds or residues derived from polymer containing gelable fluids. A filter-cake typically interferes with the production of a subterranean formation by filling the rock matrix pores, thereby inhibiting the flow of fluids from the matrix. Filter-cakes may also serve to restrict flow in hydraulic fracture proppant beds and other flow channels.

In addition to formation damage caused by filter-cake formation, well treatments and drilling operations utilizing polysaccharides may also result in the deposition of relatively viscous fluids and residues within a productive zone which create damaging conditions similar to those created by filter-cakes. Thus, formation damage may be related to filter-cake, filtrate, residues and other related materials that invade a productive zone. As a result, it is often necessary to apply stimulation treatments to bypass this drilling fluid damage in such intervals.

In the practice of drilling wells in horizontal or highly deviated configurations, as well as multi-lateral completions, wells are drilled in order to contact more hydrocarbon-bearing pay zone area within a single well in order to maximize productivity. By "deviated" it is meant that at least a portion of a wellbore has an angle of between about 0° and about 90° from the vertical, and by "highly deviated" it is meant that at least a portion of a wellbore has an angle of between about 45° and about 90° with respect to the vertical. Such wellbores often penetrate thousands of feet of productive zone as opposed to the tens to hundreds of feet contacted in vertical well configurations. Consequently, productivity damage created by polysaccharide filter-cakes, residues, and/or filtrates is exacerbated over long productive intervals within these types of well configurations.

Insufficient degradation of polysaccharide-induced damage may significantly impede flow capacity at the wellbore wall. Such reduced flow capacity may result in significant reduction of the productivity or infectivity of vertical and horizontal wells. In horizontal or highly deviated wells in particular, it is important that formation damage from drilling fluid leakoff and filter-cake deposition be mitigated or eliminated to realize the full potential of these types of completions. Furthermore, obtaining zonal isolation with cement in the presence of a filter-cake and/or residue is often difficult because these layers interfere with formation of a pressure seal between a wellbore and a production pipe string. This may occur when the presence of filter-cakes or residues between a borehole wall and pipe string blocks circulation or placement of cement in the annular area between the borehole and the casing or between two strings of pipe, thereby creating pockets of filter-cake, residue, or other non-cement materials which may result in fluid communication in the annular area between the pipe string and borehole wall or between the two pipe strings that the cement is supposed to isolate. In a completed well this may result in a loss of hydraulic integrity due to fluid movement through a filter-cake, residue layer, or other pocket underneath the cement sheath of a completed well.

A common approach to minimizing formation damage from filter-cake, filtrates, and residues has been to apply acid or strong oxidative breaker systems to dissolve filter-cake solids and polymers. A typical wellbore treatment to remove such damage consists of hydrochloric acid solutions, solutions of lithium or sodium hypochlorite, or highly concentrated solutions of conventional oxidizers like ammonium persilofate or perborate. Although acids and oxidative solution washes appear to perform reasonably well in a laboratory environment where contact of filter-cake damage with a reactive solution is easily achieved, application of these solutions may not be effective for removing the damage in horizontal intervals. For example, field experience has demonstrated that acids and oxidative solutions used to remove mud filter-cake damage have proven relatively ineffective based upon well performance. The problem is particularly evident when such treatments are applied in extended length openhole intervals. One rationale that has been proposed to explain this problem is the difficulty of contacting filter-cake materials with these reactive solutions. For example, studies have indicated that polymer coated carbonate particles used for weighting and fluid loss control may be resistant to acid attack and prevent complete removal of a filter-cake. See Burnett, D. B. "Using a Physical Wellbore Model to Study Formation Damage Problems in Well Completions," paper SPE 27393 presented at the 1994 International Symposium on Formation Damage Control, Lafayette, February 9–10.

Additional concerns regarding the use of acidic or oxidative cleanup treatments include the reactivity with tubulars which may result and elevated iron concentrations being injected into the reservoir in a manner which may promote sludging problems.

A typical polysaccharide employed in well fluids is xanthan. Xanthan containing fluids are known to cause damage to the permeability of the near wellbore area due to leakoff and mud or polymer filter-cake buildup on the formation faces in the same manner as other polysaccharides, such as celluloses and starches. Xanthan is a biopolymer that may be produced by a bacterial fermentation. It is a heteropolysaccharide of which the structure consists of a linear chain of D-glucose units that are bonded together by 1, 4-β-glucosidic linkages with trisaccharide substituents attached to the glucose backbone by β 1-3 glycosidic or mannosidic linkages. Xanthan may be used in a variety of industrial applications, for example, as described by Jeanes, "Applications of Extracellular Microbial Polysaccharide-Polyelectrolytes: Review of Literature, Including Patents," *J Polym. Sci.,* Polym. Symp. No. 45, pp. 216–221, 1974; and in, for example, U.S. Pat. No. 4,119,546. Typical well applications include, but are not limited to, those mentioned above, most typically as a brine thickener in drilling muds and workover fluids, as a viscosifier in hydraulic fracturing and cementing, as a gel blocking agent in gravel packing and frac packing operations, in secondary and tertiary recovery operations, and in non-petroleum applications such as a clarifier for use in refining processes. As previously described, conventional acid and oxidizer treatments to reduce polymeric damage are typically ineffective to remove or mitigate xanthan damage due to the resistance of xanthan towards oxidizers and acids. Although well treatments using xanthan-specific enzymes have been proposed to treat xanthan polymer damage, these treatments employ enzymes that are typically not effective at temperatures greater than about 150° F. Because many wells have downhole temperatures exceeding 150° F., proposed enzyme treatments for removing xanthan damage would be ineffective in many wells having temperatures exceeding this level.

In some wellbore related applications, it is desirable to reduce the viscosity of xanthan-containing fluids. For example, during hydraulic fracturing, a sand laden fluid is injected into a wellbore under high pressure. Once the natural reservoir pressures are exceeded, the fracturing fluid initiates a fracture in the formation which generally continues to grow during pumping. The treatment design generally requires the fluid to reach maximum viscosity as it enters the fracture which affects the fracture length and width. This viscosity is normally obtained by the gelation of suitable polymers, such as xanthan, which in this capacity are known as fracturing gels. The gelled fluid can be accompanied by a propping agent which results in the placement of the propping agent within the fracture thus produced. The proppant remains in the produced fracture to prevent the complete closure of the fracture and to form a conductive channel extending from the wellbore into the formation being treated once the fracturing fluid is recovered. Propping agents include a wide variety of material and may be coated with resins. The gel fluids may also contain other conventional additives common to the well service industry such as surfactants, and the like.

In another example, production from wellbore operations must cease temporarily to perform auxiliary procedures called workover operations. The use of temporary blocking gels, also formed by gelation of appropriate polysaccharides such as xanthans, produces a relatively impermeable barrier across the production formation. These gels may also be used as diverting agents during stimulation treatments. In this capacity, the gels are typically pumped into a formation ahead of a stimulation fluid, such as acid. The gels selectively enter the more permeable zones of the formation where they create a relatively impermeable barrier across the more permeable zones of the formation, thus serving to divert the stimulation fluid into the less permeable portions of the formation. After such a treatment the gel barrier may be broken internally or externally to allow production from, or injection into, both zones of the formation. In other cases, such blocking gels may be used in a similar manner to block the production or injection of water in secondary recovery operations by gel treatments of injection and/or production wells.

In still another example, uncrosslinked xanthan-containing polysaccharides are used thicken fluids and control fluid loss. In this capacity they may be used with proppants, such as sand control fluids and completion fluids, such as those for gravel packing. Gravel packing controls sand migration from unconsolidated or poorly consolidated formations through the placement of a gravel pack around a slotted or perforated liner or screen liner inserted at a specific location within a perforated wellbore. The "gravel" is usually sand or a very fine gravel that excludes the formation sand from entering the wellbore. Xanthans are typically used to thicken the fluids in order to properly pack gravel into the perforations of the wellbore. Although unthickened slurries pack an annulus well, the sand compacts quickly and may not have sufficient time to flow into and completely pack the perforations.

In the above examples the viscosity of xanthan-containing fluids, whether crosslinked or not, is most often desirably reduced at the end of an operation. At the end of fracturing or workover operations for example, the gels are degraded and the fluids are recovered. Gel fluids are recovered by reducing the viscosity of the fluid to a low value such that it flows naturally from the formation under the influence of formation fluids and pressure. This viscosity reduction or conversion of gels is referred to as "breaking" and is often accomplished by incorporating chemical agents, referred to as breakers, into the initial gel.

A similar reduction of the fluid viscosity of uncrosslinked, xanthan-containing fluids occurs at the end of completion operations. For example, at the end of gravel packing, the viscosity is reduced to allow the settlement of sand to properly pack the annulus. Therefore in this disclosure, "breaking" refers to the reduction of viscosity of a xanthan-containing fluid, whether crosslinked or uncrosslinked, to a low value such that it flows from the formation under the influence of formation fluids and pressure.

In addition to the importance of providing a breaking mechanism for the fluid which facilitates recovery of the fluid and resumes production, the timing of the break is of great importance. Gels that break prematurely can damage the production zone through the leak-off of contaminating materials into the production formation. If the viscosity is reduced prematurely during gravel packing, the sand settles before being properly placed within the wellbore and perforations, thus contributing to the problem of sand within the wellbore.

On the other hand, fluids that break too slowly can cause slow recovery of the fluid from the production formation. Slow recovery delays the resumption of the production of formation fluids and can cause improper packing the annulus during gravel packing. Incomplete gel degradation causes a build up of residue which interferes with production from the formation.

For purposes of the present application, premature breaking means that the viscosity diminishes to an undesirable extent prior to the end of the operation. In the typical case, it is desirable for a viscosity to remain in the range from about 60% to about 100% for the length of time required to complete the operation. However, in other cases, lower viscosities during this time are acceptable. Since some operations require extended periods of time before completion, the fluids should be capable of remaining appropriately viscous during that time period. In the laboratory setting, viscosity is measured using a rotational viscometer such as a Fann "35VG" meter or a Brookfield "DVII" digital viscometer.

For practical purposes, the viscosity of the xanthan-containing fluid should be completely reduced within a specific period of time after completion of the operation. This period of time depends on the temperature of the formation. Optimally, a gelled fluid breaks when the operation concludes. A completely reduced fluid means one that may be flushed from the formation by the flowing formation fluids and/or formation pressures. Desired characteristics of a substantially broken, uncrosslinked gel varies according to the permeability of a particular formation. However, for most formations such a broken gel regains greater than about 65% of the initial permeability of a formation sample using a gel damage permeability test.

Enzyme systems are known to degrade the types of polysaccharides used in fracturing and blocking gels as well as in other applications. Enzyme breaker systems have been designed to break gelled fracturing and blocking fluids used in the industry as well as filter-cakes. See for example U.S. Pat. Nos. 5,224,544; 5,247,995; 5,201,370; 5,562,160; and 5,566,759. Xanthan enzyme systems described in these references degrade xanthan-containing fluids at low to moderate temperatures of up to about 150° F. However, these enzyme systems are less effective at temperatures above about 150° F.

Xanthan-based well fluids are also stored and maintained on the surface. For example, xanthan containing drilling mud may be stored and maintained within a reserve pit, mud pit, or frac tank. In such cases the drilling mud typically contains a relatively large solids content, including drilled solids and solid weighting materials. After a well is drilled or a remedial well operations is completed, large volumes of xanthan containing drilling materials may remain on the surface within reserve pits or other similar storage areas. In order to remove these fluids after a well operation, the solid materials must be separated from the liquid phase. This is often difficult due to the presence of polymeric viscosifiers such as xanthan. Separation typically requires processing through separation equipment including cyclone separates, decanter centrifuges, shakers and the like, as well as the use of a large volume of water.

Xanthan-based fluids are also used in high temperature non-well applications. For example, xanthan may be used in industrial processes such as in clarification steps of a refining process. In this and other similar applications, xanthan-based filter-cakes and residues may accumulate on porous permeable media or other areas of process equipment. These filter-cakes and residues need to be degraded and removed periodically or on a continuous basis. As in well applications, xanthan-based filter-cakes and residues are difficult to remove under high temperature process conditions, and enzyme systems are typically limited to temperatures of about 150° F. In the past, steam is one method that has been employed to remove xanthan filter-cakes and residue from process flow equipment, such as in refining processes.

Consequently, a need exists for effective methods and compositions for removing xanthan-based damage from a well. In particular, a need exists for a method for stimulating productivity of a subterranean formation damaged by drilling and other fluids containing xanthan molecules at temperatures exceeding about 150° F. A need also exists for a method of improving cementing and other well treatment performance by removing areas of xanthan-based filter-cake and/or residues at temperatures exceeding about 150° F. A need also exists for an enzyme breaker or system which is effective to degrade xanthan-containing fluids at temperatures exceeding about 150° F. Further, a need exists for a method of degrading xanthan-based fluids, filter-cakes and residues in process flow systems having similar high temperatures.

SUMMARY OF THE INVENTION

In one respect, this invention is a method for degrading xanthan molecules, including the step of contacting the molecules with xanthanase enzyme complex produced by a soil bacterium bearing the ATCC No. 55941 under conditions such that at least a portion of the molecules are degraded.

In another respect, this invention is a method of treating xanthan-containing formation damage present in a wellbore or a subterranean formation penetrated by the wellbore, including the step of introducing into the wellbore a well treatment fluid comprising xanthanase enzyme complex produced by a soil bacterium culture bearing ATCC No. 55941 under conditions such that at least a portion of the xanthan-containing formation damage is degraded.

In another respect, this invention is a method of reducing the viscosity of xanthan-containing fluid by degrading xanthan molecules contained within the xanthan-containing fluid, including the step of combining the xanthan-containing fluid with an xanthanase enzyme complex produced by a soil bacterium culture bearing ATCC No. 55941 under conditions such that the viscosity of the xanthan-containing fluid is reduced.

In another respect, this invention is a method of treating a well penetrating a subterranean formation and having a well surface including the step of formulating a gelable fluid by blending together an aqueous fluid, a xanthan polymer, a suitable cross linking agent to form a xanthan polymer gel, and xanthanase enzyme complex produced by a soil bacterium bearing ATCC No. 55941. The method also includes the steps of introducing the xanthan polymer gel into the well and allowing the xanthanase enzyme complex to degrade the xanthan in the polymer gel, so that the fluid may be removed from the subterranean formation to the well surface.

In another respect, this invention is a method for producing an xanthanase enzyme complex, including the step of culturing a bacterium bearing ATCC No. 55941 in a medium containing xanthan molecules under conditions suitable for the growth of the bacterium and for the production of xanthanase by the bacterium. The method also includes the step of recovering the xanthanase from the medium.

In another respect, this invention is an isolated and biologically pure microbial culture obtained from the culture bearing ATCC No. 55941.

In another respect, this invention is an xanthanase contained in, or produced from, a solution comprising a culture bearing ATCC No. 55941.

DESCRIPTION OF ILLUSTRATIVE EMBODIMENTS

Figure 1:
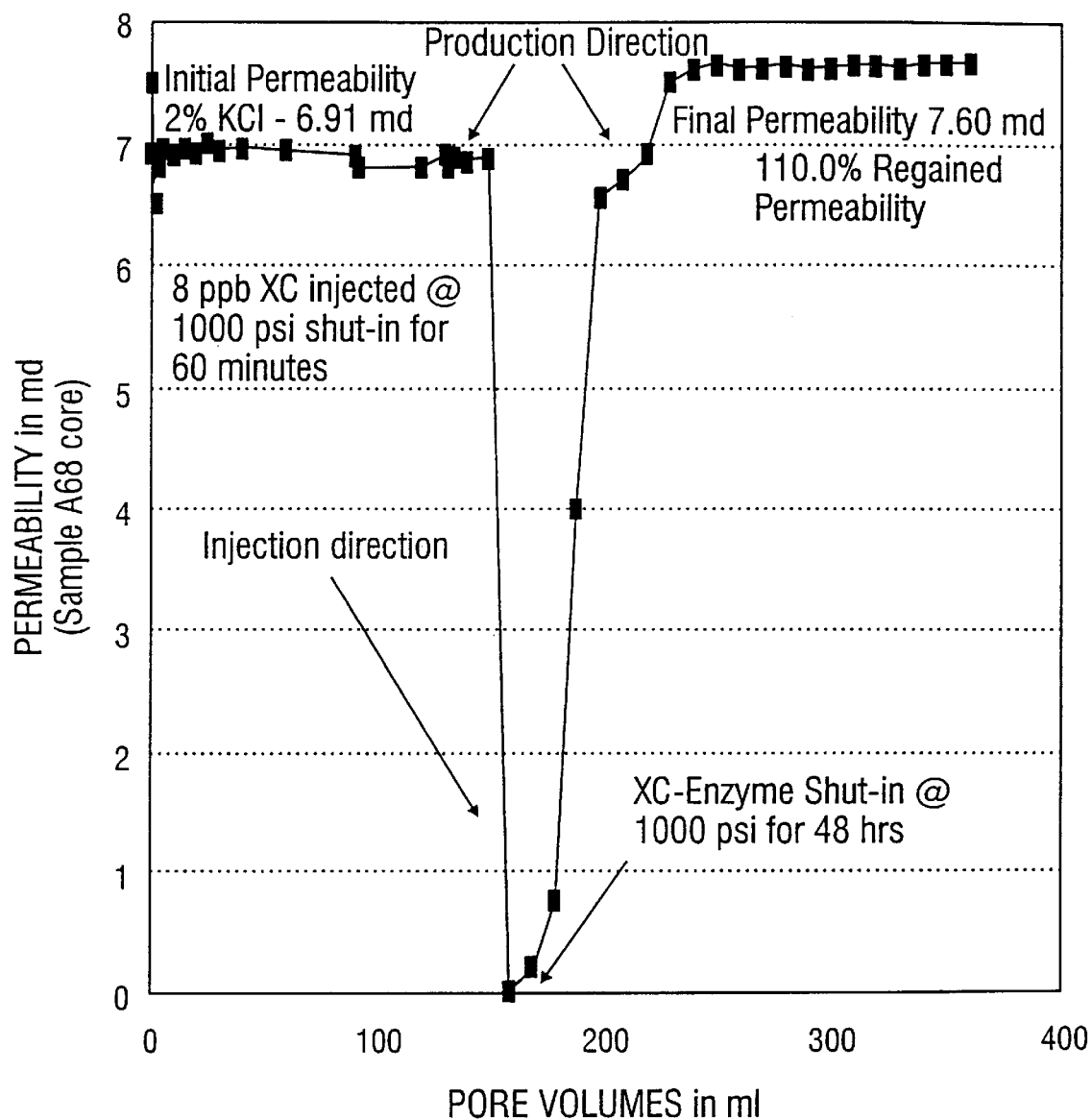
FIG. 1 illustrates permeability versus displaced pore volumes through feldspathic sandstone plug.

In the practice of the disclosed method, a polymer-linkage specific enzyme complex is used to hydrolyze or otherwise degrade xanthan-based polymer materials to non-damaging fragments. Enzymes are highly specialized proteins produced by cells and living organisms which have the ability to act as catalyst to promote specific reactions. Since, as a catalyst, the conformational structure of an enzyme is unchanged by the reaction it promotes, it may then initiate another, and so oil. Thus, the reactivity of an enzyme may be essentially infinite. In embodiments of the disclosed method, xanthan-containing materials may be combined with or contacted with xanthanase enzyme complex to cause degradation of the xanthan-containing materials. As used herein, the terms "combining", "contacting", and "applying" include any methods suitable for admixing, exposing, or otherwise causing two or more materials, compounds, or components to come together in a manner sufficient to cause at least partial degradation, partial reaction, and/or at least partial mixing to occur between the components.

Advantageously, unlike acidic or oxidative processes, polymer-linkage specific enzyme systems are substantially not reactive with substances other than targeted xanthan polymers. Therefore, many of the self-generating diversion and other problems experienced using acids or oxidative solutions are mitigated through the use of the xanthan polymer-linkage specific enzymes of the disclosed method. For example, corrosion of tubular goods and process equipment, as well as iron promoted sludging are also avoided using the disclosed polymer degradation methods and compositions. Significantly, these problems may be most pronounced at the relatively high formation and process temperatures at which previous xanthan enzymes are ineffective. Further, unlike acids or oxidative species, enzymes are inherently environmentally friendly.

In embodiments of the disclosed method and compositions, a mixed bacterial culture having ATCC No. 55941 is provided. As used herein, the terms "bacteria," "bacterium," "culture," "soil bacterium culture" and/or "microbial culture" are used interchangeably to describe the deposited bacterium bearing the ATCC No. 55941 and cultures of deposited bacterium bearing the ATCC No. 55941. This bacterium may be used to produce or elaborate a xanthanase enzyme complex which is stable and active at temperatures up to and exceeding 250° F. As used herein the "disclosed xanthanase enzyme complex" is defined to mean the xanthanase enzyme complex produced by the bacterium bearing the ATCC No. 55941. This enzyme complex has exhibited stable and active properties at temperatures up to 250° F. and under pressures up to 3,000 psi. Furthermore, this enzyme complex has exhibited improved stability as pressure increases, increased temperature stability with increasing pressure, and improved cleanup efficiency with increasing temperature. Thus, one would contemplate with benefit of this disclosure that this enzyme complex may have even greater activity and stability at pressures above 3,000 psi including 10,000 psi, and at temperatures above 250° F., including 275° F. Furthermore, as will be understood by those of skill in the art with benefit of this disclosure, temperature stability of the disclosed xanthanase enzyme complex is related to pressure, such that the maximum temperature at which the disclosed enzyme is active increases with increasing pressure. Consequently, it is within the skill of those skilled in the art to determine and/or optimize the temperature stability of the disclosed enzyme complex based on pressure, including at temperatures exceeding 250° F.

These temperature stability characteristics make the disclosed xanthanase enzyme complex ideal for degrading xanthan polymers used in well operations, such as drill-in, drilling, completion, cementing, stimulation, workover and remedial operations, which are accompanied by a wide variety of formation pressures and temperatures. This may be accomplished, for example, using operational methods in a manner as described for other enzyme compositions and/or polysaccharides in for example, U.S. Pat. Nos. 5,126,051; 5,165,477; 5,224,544; 5,247,995; 5,201,370; 5,562,160; and 5,566,759 which are incorporated herein by reference.

The disclosed enzyme complex is also useful in degrading, breaking, and/or reducing the viscosity of xanthan-containing fluids in non-wellbore applications, such as in the surface remediation of well fluids or process fluids at atmospheric pressure and in any other industrial application, particularly those applications involving relatively high temperatures and/or pressures as described above. Although use of this enzyme complex is particularly advantageous at relatively high temperatures and pressures it will be understood with benefit of this disclosure that benefits of the disclosed method and enzyme compositions may also be realized at lower pressures and temperatures, and under any condition in which it may be suitably applied to degrade, break or otherwise reduce the viscosity of any type of xanthan-containing fluids,

Bacteria Culture and Enzyme Production

The disclosed xanthanase-producing mixed microbial culture has demonstrated the capacity to produce heat stable extracellular enzymes that degrade xanthan in both ordered and unordered conformations. This mixed culture has been deposited in the ATCC in Rockville, Md. under the number 55941, and has a deposit date of Mar. 3, 1997. This culture has been identified by the ATCC using BIOLOG as a mixed culture having a Gram negative large colony of *Citrobacter freundii* and a Gram positive small colony of *Enterococcus faecalis*.

The disclosed mixed bacterial culture, ATCC 55941, was originally isolated from soil by enrichment techniques. Nutrient media for enrichment of this bacteria may be any suitable nutrient media containing xanthan as the primary carbon source or other media including, but not limited to, other polysaccharides. A typical nutrient media used for enrichment comprised xanthan, 0.3–0.5%; ammonium sulfate, 0.02–0.08%; yeast extract, 0.015–0.03%; tryptone, 0.015–0.03%; and sodium chloride, 0.3–0.5%. The initial medium utilized for enrichment techniques is set forth in Table 1 below. Soil samples were taken from several locations and added to the above broth and incubated at 75° F., 100° F., and 125° F. until viscosity reduction is observed, within 8–10 weeks. Viscosity reduction was observed from one particular soil sample incubated at 125° F. This culture then underwent multiple additional transfers to confirm xanthan biodegradation. The mixed culture was stored on agar plates or in liquid broth at 4° C. Liquid broth storage is typically desirable for routine studies because cell growth may be achieved in a shorter period of time than with the other methods.

TABLE 1

| | % w/v |
|---|---|
| Xanthan | 0.5% |
| (NH$_4$)$_2$SO$_4$ | 0.05% |
| Yeast Extract | 0.025% |
| Tryptone | 0.025% |
| NaCl | 0.5% |
| Distilled water | 98.9% |

Selective measures were then adopted to select for the ability of this culture to produce extreme heat and high pressure tolerant enzyme complexes. Cultures were begun in a new media as listed in Table 2 below. Initial culturing conditions were 75° F. at a pH of 6.3. As each subculture was performed, every 2–3 day period, or depending upon viscosity degradation, the incubation temperature was raised half a degree. This selection process took place in a BIOFLO "3000" fermenter under strictly controlled conditions. It was discovered along the course of enrichment culturing that the disclosed mixed culture produced enzymes that performed significantly better, based on viscosity reduction, in the absence of NaCl so it was dropped from the media formulation in the selection process.

TABLE 2

| | % w/v |
|---|---|
| Xanthan | 0.5% |
| (NH$_4$)$_2$SO$_4$ | 0.05% |
| Yeast Extract | 0.025% |
| Tryptone | 0.025% |
| Distilled water | 98.9% |

In one embodiment, optimized enzyme production from the disclosed bacterium bearing the ATCC No. 55941 may be accomplished by incubation in a media formulation listed in Table 3, although other media suitable for enzyme production may be employed. Levels of xanthan is typically increased to 3–4% and yeast and peptone, at 0.2%, were included. The incubation of the mixed culture may be performed at any temperature and pH suitable for enzyme production. Typically, incubation is conducted in the temperature range of about 80 to about 85° F. (26.7–29.4° C.) and at an initial pH in the range of about 6.0 to about 7.0, typically about 82.4° F. (28° C.) and a pH of about 6.3. Under these conditions the viscosity in a production batch is substantially reduced within about 2–3 days. At higher temperatures, and in the presence of pressure, the viscosity is typically reduced within about 2 days, indicating increased enzyme activity and increased enzyme complex stability. The fermentation is aerobic and the required air flow rate will depend on vessel capacity and design, batch size, and culture requirements. Guided by growth rates and xanthanase yields, the optimum rate can be readily determined by those skilled in the art. When the enzyme yield is to be maximized, it is typical to control the conditions to within the aforementioned ranges.

TABLE 3

| | % w/v |
|---|---|
| Xanthan | 0.5% |
| Yeast Extract | 0.02% |
| Peptone | 0.02% |
| Distilled water | 99.46% |

In one embodiment, a crude enzyme preparation may be isolated from a fermentation broth by removal of the cells such as by centrifugation or filtration. If desired, the enzyme in the supernatant can then be concentrated. In this embodiment, the crude enzyme preparation has specific activity of 10,400 IU/g, which can be concentrated to, for example, 520,000 IU/g by ultrafiltration process. One IU (International Unit) is defined as the amount of enzyme activity to catalyze transformation or liberation of 1.0 micromole of substrate per minute at 25° C., 1 Atmosphere, and a pH of 5.0.

For large scale production of the disclosed enzyme complexes, the broth is typically prepared using culturing methods as described above. The broth is then typically separated by ultrafiltration using 0.1 micron NMW (nominal molecular weight) cut-off membranes to remove the bacterial cells. The enzyme complex may then be concentrated, for example, 50 times (or as otherwise desired) by ultrafiltration using a 10,000 NMW cut-off membrane. The enzyme complex as thus prepared is ready for use, alone or in a mixture with other materials, to treat xanthan using the embodiments and methods as described herein. The enzyme complex may be stored for use or used directly as so made.

Although particular embodiments of producing the disclosed xanthanase enzyme complex have been described above, it will be understood with benefit of the present disclosure that any other method of production, isolating, and/or concentrating of the enzyme complex known to those of skill in the art may be employed.

Table 4 of Example 3 depicts the results of temperature studies. As shown in Table 4, the disclosed enzyme complex exhibited stability and increased cleanup efficiencies as temperature was increased to 250° F. (121° C.).

The disclosed xanthanase enzyme complex is defined herein as an enzyme complex capable of degrading xanthan molecules. Without desiring to be bound to any particular theory, based on structural characterization of degradation products, it is believed that at least two, possibly three, enzymes activities are involved: a lyase or a hydrolase that removes terminal pyruvated D-mannose residues and a β-(1,4)-D-glucanase that cleave glucosidic linkages of backbone chain residues bearing side chains. The disclosed xanthan-specific enzyme complex is believed to be specific to degrade or cleave either the α-1,2 and/or β-1,4 glycosidic linkages of the substituent and the β-1,4 glucosidic linkages of the backbone.

Enzyme Applications

In wellbore related embodiments of the disclosed method, xanthanase complexes produced from bacterium bearing the ATCC No. 55941 are introduced into a wellbore to degrade xanthan-based formation damage in the form of filter-cakes, residues, filtrates, is and/or other permeability or productivity inhibiting materials. As used herein "formation damage" refers to the formation of skin or the reduction in productivity of a subterranean formation penetrated by a wellbore due to the plugging action of a filter-cake, residue, filtrate, other material, or any other mechanism of blocking or causing permeability reduction of a subterranean formation. In the present disclosure "introduced into a wellbore" means that the disclosed enzyme complex may be pumped, injected, poured, released, displaced, spotted, circulated or otherwise placed within a well or wellbore using any suitable manner known in the art. Typically, formation damage from xanthan-based fluids follows exposure to xanthan-based fluids blended into an aqueous fluid including, but not limited to, water, brine, aqueous-based foams, and water alcohol mixtures. Often, formation damage consists of debris left over after incomplete breaking of a gel consisting of a xanthan polymer blended into such an aqueous fluid. In any case, the disclosed method and compositions may be employed to degrade, break, and/or reduce the viscosity of xanthan-based formation damage, for example by degrading filter-cakes or residues, and/or by reducing viscosity of xanthan-based fluids, such as filtrates, present within a rock matrix.

In the practice of the disclosed method, xanthan-based formation damage may also include a cross-linking agent used in gelation. Possible cross-linking agents include cross-linking agents known to those of skill in the art. For example, gelation of hydratable polymers such as xanthan has been achieved by cross-linking these polymers with metal ions including, but not limited to, aluminum antimonies, zirconium and titanium containing compounds including the so-called organotitinates. See for example, U.S. Pat. No. 4,514,309. The disclosed method and compositions may be used to reduce the viscosity of non-cross-linked xanthan-based fluids as well. These include xanthan gums used as sand control agents, frac pack or gravel pack fluids.

As an example, in one embodiment of the disclosed method, a treatment containing the disclosed xanthanase enzyme may be employed to quickly and completely degrade xanthan-based residue found within a filter-cake or rock matrix in a wellbore. In the disclosed method, xanthan based formation damage is typically treated with an externally applied enzyme treatment fluid. The degraded residue may then be flushed from a formation by formation fluids. Because the disclosed enzyme complex is highly specific it does not substantially react or degrade materials commonly found within the subterranean formation or used in wellbore operations (such as limestone, iron, resin coated proppants, tubular goods, etc.), even at temperatures exceeding 250° F. The disclosed enzyme of the bacterium bearing ATCC No. 55941 is effective at addressing formation damage caused by xanthan gums commonly utilized in drilling fluids and other well treatment fluids. For example, the xanthanase enzyme produced by the bacterium bearing ATCC No. 55941 attacks drilling fluid filter-cake by degrading xanthan polymer material that acts as a glue holding particles such as bentonite or calcium carbonate, together. After effective degradation of xanthan materials, the soluble weighting or bridging material may then be removed, ensuring even inflow into a wellbore.

In addition to addressing formation damage induced during drilling applications by, for example, drilling mud, the disclosed methods and compositions may be employed to remove or reduce formation damage induced by other wellbore operations, such as any operation utilizing xanthan-based fluids including, but not limited to, completion fluids, workover fluids, gravel pack fluids, frac pack fluids, blocking gels, and fracturing fluids. Still other applications include using the enzyme for tailoring the viscosity of xanthan fluid suspensions for a particular use, such as thinning suspensions prior to injection into underground oil-bearing formations for assisting secondary or tertiary recovery operations. The disclosed xanthanase enzyme complex may be utilized to degrade crosslinked or non-crosslinked xanthan-based fluids as described in, for example, U.S. Pat. No. 5,566,759 and U.S. Pat. No. 5,201,370, which have been incorporated by reference. In addition, the xanthanase enzyme complex may be applied internally incorporated into a xanthan-containing fluid or material, externally applied to a xanthan-containing fluid or material, or a mixture of both as described in, for example, U.S. Pat. No. 5,566,759. For example, for crosslinked blocking gels, the typical method of using an enzyme treatment is the internal incorporation of enzyme treatment with external application of enzyme treatment. For fracturing gels and uncrosslinked fluids, the typical method of application is the internal incorporation of an enzyme treatment. For gravel packing operations, the enzyme system is typically incorporated internally in the fluid.

When the disclosed method is utilized to treat xanthan-based formation damage or fluids in a wellbore, a treatment fluid containing the disclosed xanthanase enzyme complex may be injected into the wellbore to a desired location (such as opposite a productive or injective zone) at a rate sufficient to coat the formation. When used as such, a treatment fluid may be circulated, spotted, and/or injected (or bullheaded) or otherwise introduced into a wellbore and/or a formation at a rate sufficient to coat perforations and/or formation materials and contact xanthan-based formation damage. Typically, the disclosed enzyme complex is introduced as an aqueous xanthanase treatment fluid into the wellbore. Among other things, the aqueous xanthanase treatment fluid may include any suitable aqueous liquid, such as formation brine, KCl water, seawater, calcium chloride water, ammonion chlorides or substitutes thereof, most typically KCl water. Additives may also be employed, including additives commonly employed in the oil industry, such as surfactants, chelating agents, foaming agents, etc. A treatment may also be applied as a foamed fluid. A treatment fluid containing the disclosed xanthanase complex may have any suitable pH at which the disclosed xanthanase complex is active on xanthan molecules. Although not limited to any specific pH range, such a fluid treatment typically has a pH of between about 3 and about 10, most typically between about 4 and about 5. A pH of xanthanase treatment fluid of the disclosed method may be adjusted through the use of any suitable buffer, acid or base including, but not limited to, hydrochloric acid or sodium hydroxide.

For treatment of xanthan-based formation damage within a wellbore, any treatment fluid volume suitable for degrading, breaking, or reducing viscosity of the formation damage may be employed. The volume of treatment fluid may depend on many factors, including depth of the well, length of the productive or injective interval, volume of the wellbore, severity of the formation damage, and permeability and type of the formation. Typically, a volume equivalent to from about 120% of the hole volume is employed. In addition, any suitable concentration of enzyme complex within a treatment fluid may be employed. Typically, a concentration of between about 0.5% and about 20%, most typically between about 5% and about 10% by volume, based on the total volume of an aqueous treatment fluid is employed.

In the practice of the disclosed method, a xanthanase enzyme treatment fluid containing the disclosed enzyme complex produced by the bacterium bearing ATCC No. 55941 is typically placed within a production or injection wellbore in such a way as to contact xanthan polymeric damage and initiate degradation, breaking, and/or removal of a filter-cake, residue, or other damage. Once an enzyme treatment fluid has been placed in a wellbore, the wellbore is typically for a sufficient time to allow degradation of xanthan-based formation damage by the enzyme complex. Degradation characteristics are typically dependent upon the enzyme concentration used and the bottom hole temperature. An optimal shut-in time often depends on a combination of temperature, pressure and pH, and as reaction rates may vary depending on these two variables. In addition, the concentration of enzyme complex used in a treatment fluid may be increased to reduce the time required for degradation. Typically, a pretreatment laboratory test is conducted using the xanthan-based well fluid at reservoir conditions to establish the concentration and shut-in time desirable. In most cases, a typical shut-in time is between about 24 to about 72 hours, although longer or shorter shut-in times are also possible.

In a most typical application of the present embodiment, enzyme treatment fluid is pumped through tubing to the location of the filter-cake or other xanthan-based damage within the production zone at a sufficient rate to coat the formation, for example, as disclosed in, for example, U.S. Pat. No. 5,247,995, U.S. Pat. No. 5,165,477, and U.S. Pat. No. 5,126,051, which have been incorporated by reference. Pumping assures even dispersal of enzymes for best results. Most typically, the treatment is applied by foaming, and the filter-cake or other formation damage is treated with a minimum volume of aqueous treatment fluid. For a fractured formation, a minimum volume typically is equivalent to approximately one fracture pore volume for dense and non-leaking formations, with two pore volumes being more typical. Larger volumes of aqueous treatment fluid should be used for less dense and/or leaking formations. The pore volume may be measured in any manner known to those of skill in the art. An enzyme treatment is then typically shut-in in the formation for a time sufficient to begin degrading the xanthan-based filter-cake or other formation damage. Shut-in time may vary according to the parameters as described above.

When the disclosed method is used to treat xanthan-based formation damage in extended openhole applications, including horizontal and/or deviated wellbores, treatment may be applied through coiled tubing. Most typically, a treatment fluid is pumped through coil tubing with a jetting nozzle to load the hole. Foaming of the enzyme solution is typically employed in wellbores penetrating high permeability formations in order to maintain the solution in the hole as long as possible.

In another embodiment, the disclosed xanthanase-enzyme complex produced by the bacterium ATCC No. 55941 may be employed as part of a fracturing fluid as an enzyme breaker in a manner as described for galactomannan fracturing fluids in, for example, U.S. Pat. No. 5,201,370 which has been incorporated herein by reference. When so utilized, the disclosed xanthanase enzyme complex is typically combined in a gelable fracturing fluid by blending together an aqueous fluid, a hydratable xanthan polymer, and a suitable crosslinking agent for crosslinking the xanthan polymer to form a polymer gel.

Besides xanthan-containing fracturing fluids, the disclosed xanthanase enzyme complex may be used to degrade xanthan-containing blocking gels, frac packs, gravel packing fluids and cementing fluids in a similar manner as that described for cellulose-containing polysaccharide fluids in, for example, U.S. Pat. No. 5,566,759 and U.S. Pat. No. 5,562,160, which have been incorporated herein by reference.

In another embodiment, the disclosed xanthanase enzyme complex may be used in conjunction with other well treatment fluids or operations to improve the results thereof. As used herein, "well treatment fluid" means any fluid suitable for introduction into a wellbore during drilling, completion, workover or remedial operations including, but not to limited to, stimulation fluids (such as acid-containing fluids, condensate treatment fluids, scale removal or inhibitor fluids, asphaltene inhibitor or removal fluids, fracturing fluids with or without proppant, oxidizer-containing fluids, etc.), blocking gels, gravel pack fluids, frac pack fluids, clear fluids, foamed fluids, etc. For example, in cementing operations the disclosed xanthanase may be introduced prior to a cement slurry as an is externally applied treatment fluid for the purpose of removing xanthan-based filter-cake and/or residues which may interfere with the pressure integrity of the cement once it has set, for example, as described in, for example, U.S. Pat. No. 5,165,477 and U.S. Pat. No. 5,126,051, which has been incorporated herein by reference. This may done, for example, in primary or secondary cementing operations. In primary cementing operations, a sufficient spacer of xanthanase enzyme complex may be circulated ahead of the cement slurry to remove xanthan filter-cake and residues present between a pipe string and the interior wall of the open hole. In secondary cementing operations, a spearhead of xanthanase enzyme complex may be introduced ahead of a cement slurry to degrade xanthan based materials present in perforations or annular areas, thereby clearing the way for cement slurry in these locations.

In a similar manner, the disclosed xanthanase enzyme complex produced by the bacterium bearing ATCC No. 55941 may be used to clean out or otherwise remove or degrade xanthan based materials, such as formation damage, prior to a stimulation fluid including, but not limited to, acid-containing fluids, condensate treatment fluids, scale removal or inhibitor fluids, asphaltene inhibitor or removal fluids, fracturing fluids with or without proppant, oxidizer-containing fluids, or any other type of fluid known to the art suitable for stimulating production from a subterranean reservoir or wellbore. Exposure to fluids containing xanthan-based materials, such as viscosifying agents frequently inhibit the penetration of stimulation fluids, such as acids and other treatment fluids, at the formation face. Moreover, although a problem in any well, the production capability or injection efficiency may decrease drastically in open hole, horizontal, extended reach, multilateral, and high-angle wells. These types of wells present difficult problems related to cuttings suspension and removal and, by their nature are more susceptible to formation damage. Such wells are typically designed to increase production by increasing surface area within the producing zone. To achieve the intended increased production through increased surface area, damage to formation permeability in the area of interest typically must be minimized. In conjunction with this, a special type of drilling fluids, "drill-in" fluids, have been found to be highly useful in such wells. Drill-in fluids (which are also referred to as "clean" fluids) containing low-residue producing polymers are normally employed so that potential for permeability damage is reduced. Properly utilized, drill-in fluids improve well productivity as measured by higher-than-expected production rates and improved reservoir recovery. Drill-in fluids have become very popular in the drilling of horizontal and multilateral wells due to their ability to suspend and remove cuttings. Categories of drill-in fluids include fluids comprising sized salt, specially sized calcium carbonate, conventional calcium carbonate, mixed-metal hydroxide, and specially formulated oil-based and synthetic fluids.

Drill-in fluids normally contain viscosifying polymers such as a biopolymer, biopolymer blends, derivatized starch, or derivatized cellulose. Drill-in fluids may consist of different combinations of viscosifiers. Examples of such systems include but are not limited to starch-based systems containing xanthan, cellulose-based systems containing xanthan, and mixed systems containing cellulose, xanthan and starch. Water based drill-in fluids such as sized salt fluids may contain 3 to 5 pounds of biopolymer per barrel, derivatized starch, and an additional derivatized starch to act as a filtration control agent. When such water-based fluids are employed, acid-based or oxidizer-type breaker systems have typically been incorporated to break down residual mud and filter-cake. Acid based breaker systems (typically 5 to 15% by weight hydrochloric acid) and oxidizing breakers typically do not include enzymes. Filter-cakes are formed, however, even when "clean" drill-in fluids are introduced into subterranean formations with conventional breaker systems. The disclosed xanthanase enzyme complex produced by the bacterium bearing the ATCC No. 55941 may be used to degrade xanthan materials related to the various types of xanthan-containing polymer systems which are conventionally used in drill-in fluids, or other fluids prior to stimulation treatment.

In general, using this embodiment of the disclosed method a cleanup treatment fluid is introduced into a subterranean formation by way of a wellbore. The cleanup treatment fluid is typically an aqueous-based fluid that includes, at least in part, the disclosed xanthan enzyme complex which is effective to degrade xanthan polymeric viscosifiers that may be present in the wellbore. The cleanup treatment fluid is prepared by admixing a quantity of the enzyme sufficient to degrade polymeric viscosifiers with an aqueous liquid as the carrier fluid. The aqueous liquid may be fresh water, sea water, or brine and may include additives such as buffering agents to control pH, clay stabilizers, surfactants, or other agents. The cleanup treatment fluid may also be in the form of a foam of any suitable quality, typically with a quality of greater than about 50%. Cleanup treatment fluid in such form is desirable to prevent loss of the fluid before contact with the entire wellbore is achieved. Such instances may be especially encountered in open holes or where fractures in the wellbore are to be treated. However, in certain circumstances, for example injection wells, it may not be desirable to cleanup natural fractures.

The concentration of the disclosed enzyme complex in the cleanup treatment fluid is typically any suitable amount effective to degrade the xanthan polymeric materials found in the wellbore. In general, an effective amount of the disclosed xanthanase enzyme complex is admixed with the aqueous carrier or treatment fluid which is in the range of from about 5 to about 200 gallons per thousand (gpt) of treatment fluid. The amount is typically in the range of about 50 to about 100 gallons per thousand (gpt) of treatment fluid. It may be necessary to adjust the amount to higher or lower concentrations depending on well conditions. It is within the skill in the art to optimize the amount of enzyme complex necessary to effectively degrade an xanthan polymeric viscosifier within a desired time period. The cleanup treatment fluid typically is designed to degrade the viscosifier within seven days, and more typically within about 24 to about 48 hours.

In the method of the present embodiment, after preparing a cleanup treatment fluid suitable for degrading the xanthan polymeric materials present in a particular well, the treatment fluid is injected into the well using suitable equipment. For example, It may be spotted in a wellbore having an open hole through drill pipe or injected using coiled tubing. It may also be bullheaded into the well. In the method of the present embodiment, an appropriate volume of cleanup treatment fluid is to be injected into the well which volume is determined by the size of the wellbore plus accounting for some fluid loss due to leakoff. For example, for an open hole, the volume of the open hole plus an additional volume of about 25% is believed to be an optimal amount required for filling the drilled hole and allowing for fluid leakoff of about 25%. It is also typical when spotting conventional tubing or using coiled tubing that initially the tubing extend through the entire producing interval of interest.

Once the cleanup treatment fluid is in place, the well is typically shut in to allow the cleanup treatment fluid to degrade residual polymeric viscosifiers in the wall of the bore and the surrounding formation. The time for shut-in will vary from well to well depending on temperature, fluid treatment composition and concentrations, and reservoir conditions. The most typical time for shut-in of the cleanup treatment fluid is from about 24 hours to about 48 hours. In any case, the shut-in time is typically long enough to allow total placement of the cleanup treatment fluid in the wellbore and permit contact of the cleanup treatment fluid to the exposed surface areas of the wellbore and any extensions thereof. After sufficient time has elapsed for the cleanup treatment fluid to act, the cleanup treatment fluid in certain applications may be recovered from the wellbore and formation if desired, for example by any of the fluid recovery methods previously mentioned.

In the next step of the method of this embodiment, a stimulation treatment, such as an acid treatment, is normally performed. The parameters for the stimulation treatment are designed for the particular well of interest and may depend, for example, upon whether the formation is sandstone or carbonate in nature. For example, the selection of the specific treatment parameters for such a stimulation treatment may be readily determined by one skilled in the art. In the case of acid treatments, the treatment typically includes may include one or more aqueous acid solutions and may also include additives such as corrosion inhibitors, surfactants, retarders, friction reducers, anti-sludge agents, and the like. Aqueous acids include hydrochloric, hydrofluoric, formic, and mixtures thereof, and other types of acids suitable for the particular well to be treated. Hydrochloric acid in a concentration of about three to twenty-eight percent is typically used in the method of the present embodiment, however, mixtures of hydrochloric acid with other acids may also be used. An appropriate amount of the aqueous acid is injected into the wellbore so that the portion of the well previously treated with the cleanup treatment fluid is contacted with the acid. In a typical embodiment the acid is injected in the wellbore using coiled tubing.

Alternatively, when the drill-in fluid used in the well contains sized salt instead of sized calcium carbonate as the weighting additive, it may be desirable to use an undersaturated brine after the cleanup treatment fluid to remove the sized salt so that permeability at the formation face may be increased.

The cleanup treatment fluid degrades the polymer so that solids contained in the filter-cake may be removed. After the appropriate amount of time has passed, a treatment is performed to remove the solids. It has surprisingly been discovered that by utilizing the present embodiment for injection wells the size and concentration of a stimulation treatment, such as an acid or brine treatment, may be substantially reduced while obtaining the same or greater increase in production or injectivity (when the treatment is applied to an injection well). The cleanup treatment fluid allows greater and more uniform penetration of an acid or other stimulation fluid into a formation. Therefore, this embodiment of the disclosed method may be advantageously employed to provide improved production and improved cost effectiveness by allowing reduced volumes and/or concentrations of acid to achieve the same results.

It will be understood with benefit of the present disclosure that treatment fluids comprising the disclosed enzyme complex produced by the bacterium bearing the ATCC No. 55941 may be employed during completion operations or after completion. It will also be understood that these fluids may be used on production wells as well as injection wells, both those newly completed and those that have been on production or injection for a period of time. In any case, once a treatment comprising the disclosed enzyme complex has been introduced into a well to contact and degrade xanthan-based materials, the degraded materials may be removed from the wellbore in any suitable manner if so desired. For example, degraded material may be removed by annular circulation, removed by production of formation fluids, or bullheaded into a formation.

An xanthanase-enzyme based treatment fluid may be prepared in any suitable manner known to those of skill in the art.

The disclosed xanthanase enzyme complex produced by the bacterium bearing ATCC No. 55941 may also be utilized in degrading xanthan-based materials in non-wellbore applications. For example, it may be utilized in the degradation, breaking, and/or viscosity reduction of xanthan-based materials present in well treatment fluids or other industrial fluids that are present on the surface, rather in a wellbore. For example, these non-wellbore applications include, but are not limited to, treatment to reduce viscosity of fluids containing xanthan-based materials present in surface storage facilities including, but not limited to, mud pits, surface vessels, mud tanks, frac tanks, conventional storage tanks, process vessels, etc., for example as described in, for example, U.S. Pat. No. 5,165,477 and U.S. Pat. No. 5,126,051 which have been incorporated herein by reference. In such cases, the temperature of the xanthan-based fluid may be adjusted to facilitate degradation and/or viscosity reduction. Typically, the temperature of an xanthan-containing fluid may be adjusted to a value in the range of from about 75° F. to about 120° F., more typically to a value in the range from about 80° F. to about 100° F. Other non-wellbore applications of the disclosed xanthanase enzyme complex include degradation, breaking, or viscosity reduction of xanthan-based fluids used in industrial applications including, but not limited to, xanthan-based clarifying fluids used in high temperature refining operations.

EXAMPLES

The following examples are illustrative and should not be construed as limiting the scope of the invention or claims thereof.

The laboratory techniques used in some of the following examples were developed to simulate and characterize possible damage caused by drilling muds. A number of different test procedures were used to determine effectiveness of breaker systems in degrading polymeric filter-cakes generated by drilling and/or well treatment fluids. The laboratory procedures used in these examples were designed to simulate downhole conditions. These tests included wellbore filter-cake removal and core flow/permeability restoration testing.

Example 1
Optimized Production and Recovery of Enzyme

The medium listed in Table 3 was used for optimum production of the enzyme complex produced from the bacterium bearing the ATCC No. 55941. Initial or first stage culturing was performed with a 10% v/v inoculation. Incubation temperature is 28° C. for 2–3 days or until viscosity reduction is observed and bacterial growth is apparent. The fermenter or second stage culturing was carried out with a. 3–5% v/v inoculation. The temperature was controlled at 28° C. for 2–3 days or until sufficient viscosity reduction. Enzymes produced under these culturing conditions exhibited temperature stability at 121° C. with 500 psi pressure and were found to have a molecular weight greater than 10,000 daltons. In this laboratory enzyme production method, fermentation broth from the mixed culture was centrifuged to remove the bacterial cells. The broth was then filtered by tangential flow with membranes of various nominal molecular weight cut-off limits. Further testing revealed the molecular weight of the enzyme complex was in the greater than 10,000 daltons range.

For large scale production of the disclosed enzyme complexes, the broth was prepared using culturing methods as described above. The broth was then separated by ultrafiltration using 0.1 micron NMW (nominal molecular weight) cut-off membranes to remove the bacterial cells. The enzyme had a specific activity of 10,400 IU/g. The enzyme complex as thus prepared is ready for use, alone or in a mixture with other materials, to treat xanthan using the embodiments and methods as described herein. The enzyme complex may be stored for use or used directly as so made.

Although particular embodiments of producing the disclosed xanthanase enzyme complex have been described above, It will be understood with benefit of the present disclosure that any other method of production, isolating, and/or concentrating of the disclosed enzyme complex known to those of skill in the art may be employed.

Example 2
Altered Method of Enzyme Production

Fermentation broth from the mixed culture bearing the ATCC No. 55941 was clarified by filtering first through a 10 micron and then a 0.2 micron filter to remove bacterial cells. The clarified broth was then concentrated using tangential flow filtration to 10,000 nominal molecular weight limit.

Example 3
Wellbore Filter-Cake Removal

A modified high breaker system temperature high pressure (HTHP) fluid loss cell was used to evaluate the filter-cake removal efficiency of the breaker systems. Several breaker systems, including incorporating the disclosed xanthanase enzyme complex bearing the ATCC No. 55941. This apparatus was chosen because of the ability to approximate the downhole conditions. The formation face was simulated by placing a Berea sandstone disc of known permeability into the cell. In each test, an xanthan filter-cake was built on the sandstone face. The drilling fluid breakers evaluated included the disclosed xanthan-linkage specific enzyme complex, 5% lithium hypochlorite and 6% sodium hypochlorite. The tests were performed at temperatures ranging from 150° F. (65° C.) to 250° F. (121° C.) using modified API RP39 procedures as described in Beall et al., "Evaluation of a New Technique for Removing Horizontal Wellbore Damage," paper SPE 36429 presented at the SPE 71th Annual Technical Conference and Exhibition, Denver, Oct. 6–9, 1996.

The results of wellbore filter-cake removal testing on drilling fluids is shown in Table 4 and 5. The drilling fluid used in tests 1–6 consisted of 8.0 pounds per barrel (ppb) xanthan ("XC") polymer only. Tests 1–3 were conducted at 150° F. with 50 md Berea core discs. The oxidative breakers provided cleanup efficiencies ranging from 32% for a 6% sodium hypochlorite solution to 54% for a 5% Lithium hypochlorite solution following 24-hour shut-in times. The xanthanase enzyme breaker system was observed to provide a 85% cleanup efficiency after a similar 24-hour shut-in time indicating superior degradation and/or removal of the xanthan.

Tests 4–6 were conducted at 175° F., 200° F. and 250° F. mainly to evaluate the cleanup efficiency of the disclosed xanthan enzyme breaker at elevated temperatures. Significantly at a temperature of 250° F., the disclosed xanthanase enzyme complex exhibited its highest cleanup efficiency of 96%. This data indicates the disclosed invention performs well at a temperature of 250° F. The data also suggests that the disclosed xanthanase enzyme complex performs at a higher efficiency as the temperature increases, and is thus expected to perform well at temperatures well in excess of 250° F. under suitably high pressures.

TABLE 4

Wellbore Filter-Cake Removal

| Test | 1 | 2 | 3 | 4 | 5 | 6 |
|---|---|---|---|---|---|---|
| Disc Permeability | Berea 50 md | Berea 50 md | Berea 50 md | Berea 50 md | Berea 50 md | Berea 50 md |
| Mud Type | Xanthan | Xanthan | Xanthan | Xanthan | Xanthan | Xanthan |
| Breaker | NaOCl | LiOCl | XC-Enzyme | XC-Enzyme | XC-Enzyme | XC-Enzyme |
| Carrier Fluid | 2% KCl | 2% KCl | 2% KCl | 2% KCl | 2% KCl | 2% KCl |
| Temperature | 150° F. | 150° F. | 150° F. | 175° F. | 200° F. | 250° F. |
| Shut-In Time | 24 hrs | 24 hrs | 24 hrs | 24 hrs | 24 hrs | 24 hrs |
| Cleanup Efficiency | 32% | 54% | 85% | 94% | 92% | 96% |

The drilling fluid used in tests 7–12 of Table 5 consisted of 8.4 ppb XC polymer and 15.0 ppg calcium carbonate. Filter-cakes were created on the Berea disc in a manner previously described. In each of the tests, the filter-cakes were treated with a breaker as indicated in Table 5 according to the method previously described. As shown in Table 3, the disclosed xanthan enzyme complex are reserved to provide an average of 97% cleanup efficiency with a 48 hour shut-in. The testing was conducted at 154° F. with 50 md Berea discs. The disclosed xanthan enzyme complex was observed to provide an average a 97% cleanup efficiency with a 48-hour shut-in. Test 12, in which a light crude oil was mixed with the polymer, indicates that compatibility problems are not encountered when the enzyme system comes in contact with hydrocarbons.

TABLE 5

Wellbore Filter-Cake Removal

| Test | 7 | 8 | 9 | 10 | 11 | 12 |
|---|---|---|---|---|---|---|
| Core Permeability | Berea 50 md | Berea 50 md | Berea 50 md | Berea 50 md | Berea 50 md | Berea 50 md |
| Mud Type | XC/CaCO3 | XC/CaCO3 | XC/CaCO3 | XC/CaCO3 | XC/CaCO3 | XC/CaCO3/Crude Oil |
| Breaker | None | LiOCl | XC-Enzyme | XC-Enzyme | XC-Enzyme | XC-Enzyme |
| Carrier Fluid | 2% KCl | 2% KCl | 2% KCl | 2% KCl | 2% KCl | 2% KCl |
| Temperature | 154° F. | 154° F. | 154° F. | 154° F.. | 154° F. | 154° F. |
| pH | 6.9 | 6.3 | 5.0 | 5.0 | 6.3 | 4.9 |
| Regain Permeability | 27% | 36% | 98% | 94% | 89% | 99% |

Example 4
Core Flow/Regain Permeability Testing

A core permeameter was utilized to evaluate returned permeability under dynamic conditions at 120° F. The core flow tests were performed using Feldspathic sandstone plugs consisting predominantly of quartz with small amounts of siderite ($FeCO_3$), chlorite and mica-illite. The cores were loaded into a hydrostatic holder and allowed to thermally equilibrate overnight. The cores were then flushed with a refined mineral oil to establish an irreducible water saturation. The drilling fluid used to generate the filter-cake consisted of potassium chloride and 8.0 ppb XC. Testing was performed to evaluate returned permeability.

A baseline permeability was established to be 6.91 md using 2% KCl. Next, a filter-cake was built on the injection core-face using the drilling fluid described above. Next, an enzyme treatment comprising 2% KCl and 100 gallons/thousand gallons (gpt) crude xanthan enzyme produce from bacterium bearing ATCC No. 55941 was flushed across the coreface and shut-in for 48 hours. Final permeability in the production direction was established to be 7.60 md (or 110% of the original 6.91 md value). The enzyme treatment was flushed across the coreface and shut in for 48 hours. Final permeability in the production direction approached 100% of the original 6.91 md value. This test is shown graphically in FIG. 1. This example shows regained permeability following treatment of a filter-cake with the disclosed xanthanase enzyme complex according to one embodiment of the disclosed method and compositions. The results of this example indicate effectiveness of the enzyme.

Example 5
Core Flow/Regain Permeability Comparison Testing

Using techniques similar to those employed in Example 2, regained permeability testing was performed on feldspathic sandstone plugs similar to that employed in Example 2 under dynamic conditions at 125° F. In this example, regained permeability following establishment of an xanthan filter-cake was measured with and without treatment with the present invention.

Figure 2:
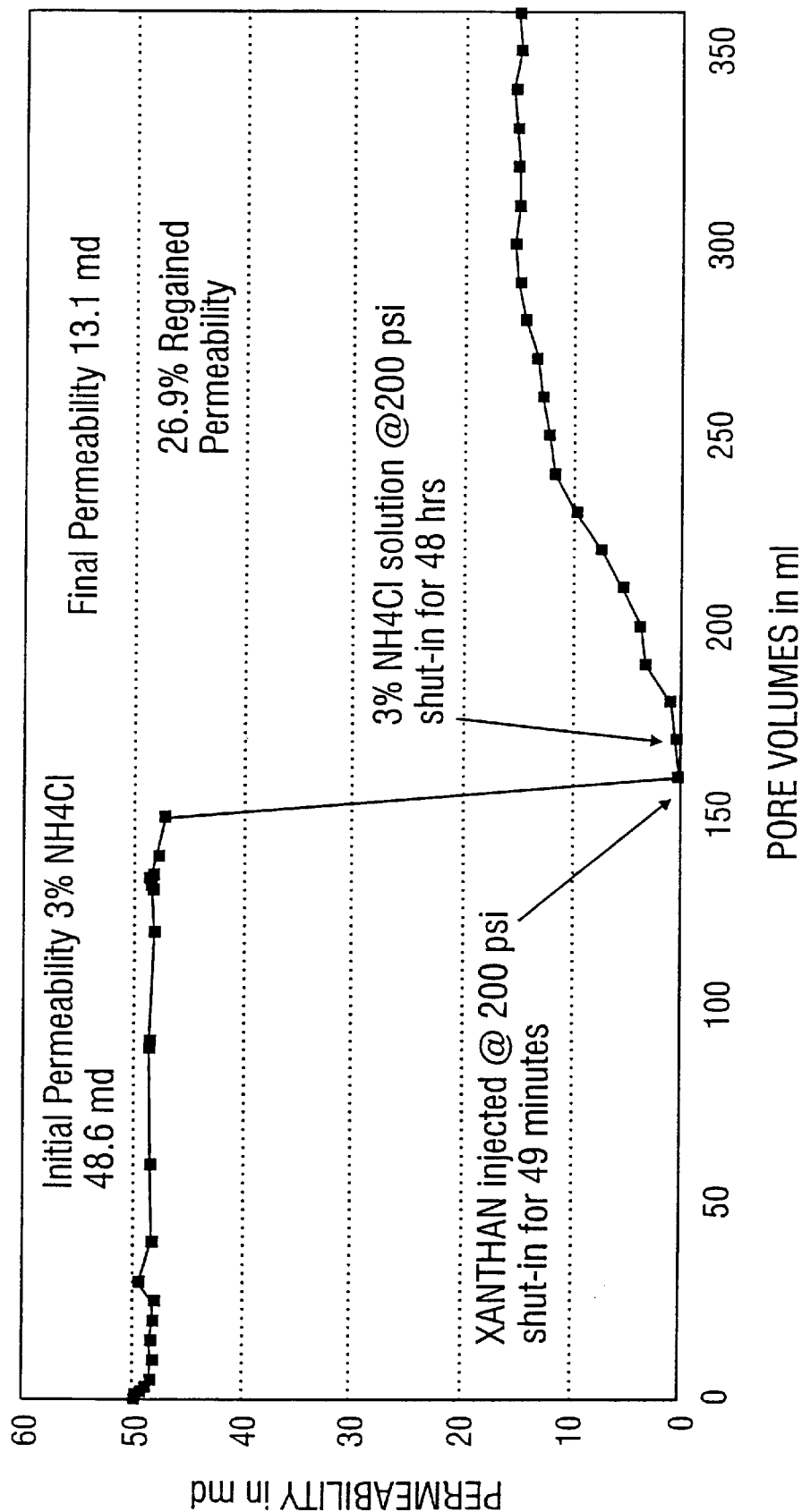
FIG. 2 illustrates permeability versus displaced pore volumes through a feldspathic sandstone plug absent a treatment according to the disclosed method.

As shown in FIG. 2, a baseline permeability of the first plug was established to be 48.6 md using 3% $NH_4Cl$. Next, a filter-cake was built on the injection core-face using xanthan-based drilling fluid injected at 200 psi. The core plug was then shut in for 49 minutes. Next, the core plug was treated in the injection direction with 3% $NH_4Cl$ is solution at 200 psi and shutin for 48 hours. Following the shut-in, the final permeability was 13.1 md (or 26.9% of the original 48.6 md permeability).

Figure 3:
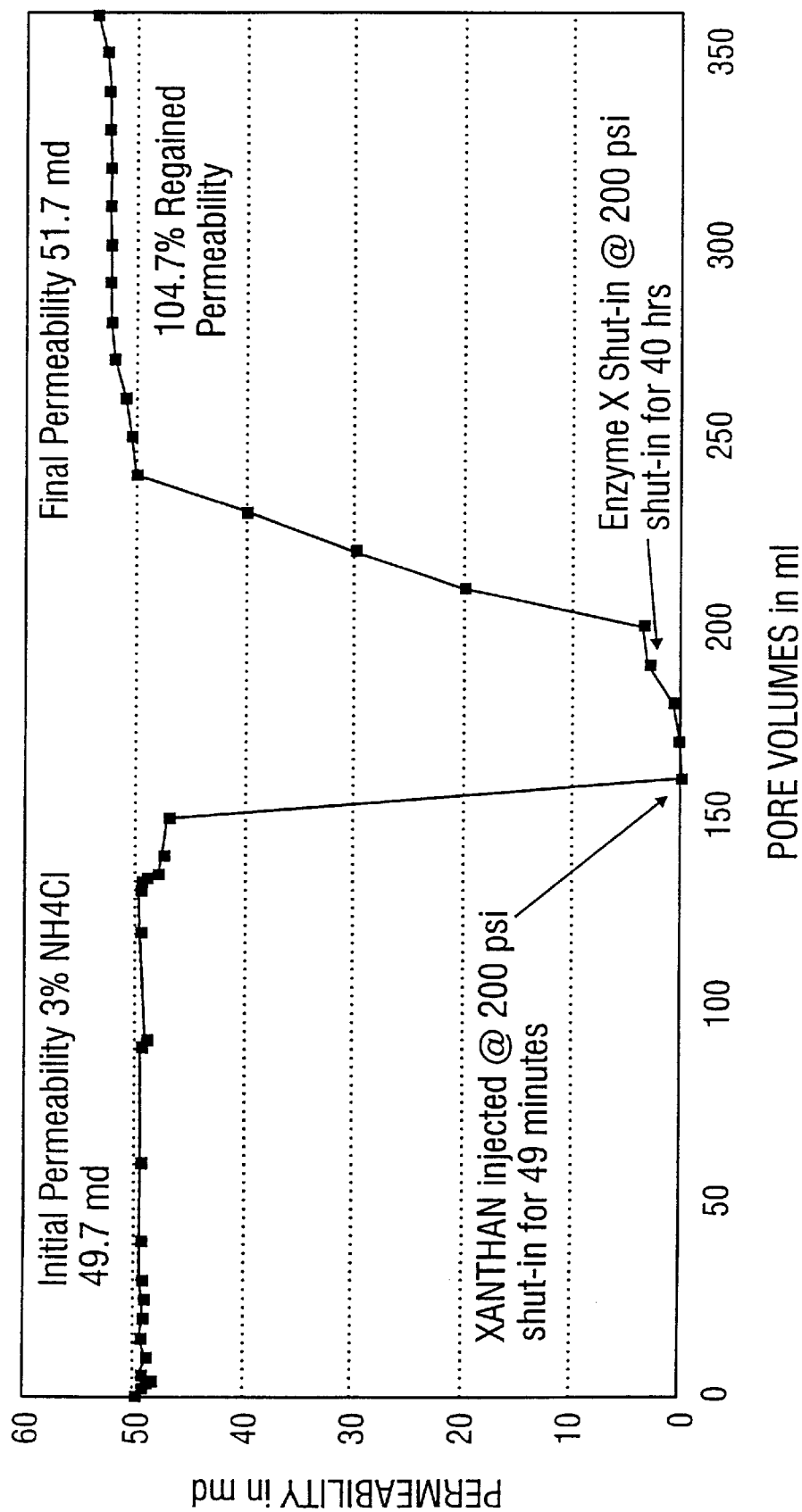
FIG. 3 illustrates permeability versus displaced pore volumes through a feldspathic sandstone plug before and after treatment according to one embodiment of the disclosed method.

As shown in FIG. 3, the initial permeability of a second core plug was established to be 49.7 md using 3% $NH_4Cl$. Next, a filter-cake was built on the injection core-face of the second plug by injecting xanthan-based drilling fluid at 200 psi, followed by a shut-in period of 49 minutes. An enzyme treatment fluid comprising 2% KCl and 100 gallons/thousand (gpt) of crude xanthan enzyme complex produced from bacteria bearing ATCC No. 55491 was then flushed across the core-face and shut-in at 200 psi for 40 hours. Final permeability of the second core in the production direction was established to be 51.7 md (or 104.7% of the original 49.7 md value). The results of this example indicate effectiveness of the treatment.

Example 6
Case Histories

The disclosed methods and compositions were evaluated for removal of xanthan-based formation damage in a horizontal production well. Also evaluated were the results of conventional formation damage removal treatments on two off-set wells. The off-set wells were treated with either a lithium or sodium hypochlorite breaker solution.

The off-set wells consisted of 6.125-in. horizontal openhole interval of 1,270 and 1,335 ft, respectively. The bottomhole temperature in all the wells was 154° F. Drilling fluid comprised of 8 ppb xanthan polymer and 15.0 ppb of calcium carbonate was used. The first offset well was treated with 50 barrels of an aqueous solution of 6% sodium hypochlorite as a filter-cake cleanup treatment through drill pipe. The first off-set well was shut in for 12 hours following placement of the cleanup treatment. After the shut-in period, the well demonstrated an initial production ("IP") of 192 barrels of oil per day. The well stabilized at a production rate of 221 barrels of oil per day ("BOPD") after six days, but after two months had declined to 16 BOPD. The cumulative production over 60 days totaled 7,119 barrels of oil as shown in Table 6.

The second off-set well was drilled with the same drilling fluid as the first off-set well and treated with 50 barrels of a 10% lithium hypochlorite solution through drillpipe. This well was also shut in for 12 hours. This well stabilized at 366 BOPD after nine days, but had declined to 98 BOPD within 17 days and stopped producing after 29 days. The cumulative production over the life of the second off-set well totaled 4,712 barrels of oil.

The enzyme complex test well consisted of 1,100 ft of 6.125-in. horizontal openhole interval and a bottomhole temperature of 154° F. This well was drilled using the same drilling fluid as the off-set wells, consisting of xanthan polymer and calcium carbonate. In this case, an enzyme complex treatment consisting of the disclosed xanthanase enzyme complex produced by the bacterium bearing ATCC No. 55941 in 2% KCl water along with a fluid surfactant was employed. Forty barrels of the enzyme treatment fluid were needed to fill the open hole. An additional 10 bbls were mixed to account for pit volume and excess. The treatment was pumped at 4.5 BPM through drill pipe. Following a 48-hour shut-in period, the well was opened and began producing at 113 BOPD. The well stabilized at 330 BOPD after 12 days. The cumulative production of this well after 60 days was 14,670 barrels of oil.

taneous or sequential combination with other enzymes, enzyme complexes, chemical breakers, treatment fluids (well or process type) or other compositions. In addition, it will be understood that the disclosed xanthanase enzyme complex may be utilized to degrade and/or remove any xanthan containing fluid, including those fluids containing other polymers in addition to xanthan.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed bacterium, compositions and, methods may be utilized in various combinations and/or independently. Thus the invention is not limited to only those combinations shown herein, but rather may include other combinations.

What is claimed is:

1. A method for degrading xanthan molecules, comprising the step of:

contacting said molecules with xanthanase enzyme complex produced by a soil bacterium bearing the ATCC No. 55941 under conditions such that at least a portion of said molecules are degraded.

2. The method of claim 1, wherein said xanthan molecules are present in a wellbore.

3. The method of claim 1, wherein said xanthan molecules are present in an xanthan-containing aqueous fluid, and wherein a viscosity of said xanthan-containing fluid is reduced during said step of contacting.

4. The method of claim 1, wherein said step of contacting occurs at a temperature of up to about 250° F.

5. The method of claim 1, wherein said step of contacting occurs at a temperature of at least about 150° F. and at a pressure at which said enzyme complex is active to degrade said xanthan molecules.

6. The method of claim 1, wherein said step of contacting further comprises the steps of:

TABLE 6

Well Results and Cumulative Production

| Well No. | Treatment Fluid | Production Time (days) | BHST | Lateral Length | Aver. Permeability | Prod. BOPD | Cum. Barrels 60 days |
|---|---|---|---|---|---|---|---|
| 1 | 50 BBLs of 6% Sodium Hypochlorite | 1 | 154° F. | 1270 FT | 50 md | 192 | 7,119 |
|   |   | 6 |   |   |   | 221 |   |
|   |   | 15 |   |   |   | 166 |   |
|   |   | 29 |   |   |   | 96 |   |
|   |   | 60 |   |   |   | 16 |   |
| 2 | 50 BBLs of 10% Lithium Hypochlorite | 9 | 154° F. | 1335 FT | 50 md | 366 | 4,712 |
|   |   | 17 |   |   |   | 98 |   |
|   |   | 29 |   |   |   | 0 |   |
|   |   | 60 |   |   |   | 0 |   |
| 3 | 50 BBLs of Xanthan Complex Enzyme | 2 | 154° F. | 1100 FT | 50 md | 113 | 14,670 |
|   |   | 3 |   |   |   | 190 |   |
|   |   | 12 |   |   |   | 330 |   |
|   |   | 60 |   |   |   | 147 |   |

Although particular embodiments of the disclosed method and xanthanase enzyme complex have been described, it will be understood with the benefit of the present disclosure that the disclosed xanthanase enzyme complex produced by bacterium bearing the ATTC No. 55941 may be utilized in many ways and combinations, including alone or in simulforming xanthan-containing fluid by combining said xanthan molecules with an aqueous fluid and said xanthanase enzyme complex; and allowing said xanthanase enzyme complex to degrade at least a portion of said xanthan molecules such that the viscosity of said xanthan-containing fluid is reduced.

7. The method of claim 5, wherein said xanthan-containing fluid is a well treatment fluid, and further comprising the step of:

introducing said xanthan-containing fluid into a wellbore after said step of forming said xanthan-containing fluid.

8. The method of claim 1, further comprising the step of forming xanthan-containing fluid by combining said xanthan molecules with an aqueous fluid, and wherein the step of contacting comprises the steps of:

applying said xanthanase enzyme complex to said xanthan-containing fluid; and allowing said xanthanase enzyme complex to degrade at least a portion of said xanthan molecules contained in said xanthan-containing fluid.

9. The method of claim 8, wherein said step of contacting occurs within a wellbore.

10. The method of claim 8, wherein said step of contacting occurs within a refinery process stream.

11. The method of claim 8, further comprising the step of allowing said xanthan-containing fluid to form xanthan-containing filter-cake, xanthan-containing residue, or mixture thereof prior to said step of applying; and wherein said step of applying further comprising the steps of:

applying said xanthanase enzyme complex to said xanthan-containing filter-cake, xanthan-containing residue, or mixture thereof; and allowing said xanthanase enzyme complex to degrade at least a portion of said xanthan molecules contained in said xanthan-containing filter-cake, xanthan-containing residue, or mixture thereof.

12. The method of claim 11, wherein said filter-cake residue or mixture, is found within a subterranean formation which surrounds a well bore, and further comprising the steps of:

allowing production fluids to flow from said well bore;

reducing the flow of said production fluids from said formation below expected flow rates prior to said step of applying; and removing the degraded filter-cake from said subterranean formation to the well surface after said step of applying.

13. The method of claim 11, wherein said filter-cake, residue or mixture is found within a wellbore, and further comprising the step of introducing cement into said wellbore after said step of allowing.

14. The method of claim 11, wherein said filter-cake, residue or mixture is found within a wellbore, and further comprising the step of introducing a second well treatment into said wellbore after said step of allowing.

15. The method of claim 14, wherein said second well treatment fluid comprises a stimulation fluid.

16. The method of claim 1, wherein said xanthan molecules have repeating units of glucose linked by β-1-4 glucosidic linkages, and wherein said xanthanase enzyme complex attacks said β-1-4 glucosidic linkages.

17. The method of claim 1, wherein said xanthan molecules are present in a fluid containing solid particulate materials stored in a surface storage facility, and further comprising the steps of:

allowing said solid particulate materials to settle in said surface facilities after said step of contacting.

18. The method of claim 17, wherein said fluid is a well treatment fluid.

19. A method of treating xanthan-containing formation damage present in a wellbore or a subterranean formation penetrated by said wellbore, comprising the step of:

introducing into said wellbore a well treatment fluid comprising an xanthanase enzyme complex produced by a soil bacterium culture bearing ATCC No. 55941 under conditions such that at least a portion of said xanthan-containing formation damage is degraded.

20. The method of claim 19, wherein at least a portion of said wellbore is openhole, wherein at least a portion of said formation damage is present in said openhole, and wherein said step of introducing comprises introducing said well treatment fluid into said open hole.

21. The method of claim 19, wherein said step of introducing comprises introducing said well treatment fluid into said wellbore through a concentric string of pipe positioned within said wellbore.

22. The method of claim 19, wherein at least a portion of said wellbore is horizontal or deviated at an angle of greater than about 45° from the vertical.

23. The method of claim 19, wherein said well treatment fluid comprises said xanthanase enzyme complex in an aqueous fluid.

24. The method of claim 19, wherein said xanthan formation damage comprises an xanthan-containing filter-cake or residue, and wherein said step of introducing further comprises the steps of:

injecting said well treatment fluid to a desired location within said wellbore;

allowing said xanthanase enzyme complex to degrade said xanthan formation damage such that said formation damage may be removed from said wellbore or subterranean formation to the well surface.

25. The method of claim 19, further comprising the step of introducing cement into said wellbore after said step of introducing said well treatment fluid comprising an xanthanase enzyme complex.

26. The method of claim 19, wherein said formation damage exists in an annular area between an interior surface of said wellbore and a string of pipe present in said wellbore; wherein said step of introducing comprises the step of circulating said well treatment fluid through said annular area to remove at least a portion of said formation damage; and further comprising the step of:

introducing cement into said annular area to cement said pipe string in said wellbore.

27. The method of claim 19, further comprising the step of introducing a second well treatment fluid into said wellbore after said step of introducing said xanthanase well treatment fluid into said wellbore.

28. The method of claim 27, wherein said second well treatment fluid comprises a stimulation fluid.

29. A method of reducing a viscosity of an xanthan-containing fluid by degrading xanthan molecules contained within said xanthan-containing fluid, comprising the step of combining said xanthan-containing fluid with an xanthanase enzyme complex produced by a soil bacterium culture bearing ATCC No. 55941 under conditions such that said viscosity of said xanthan-containing fluid is reduced.

30. The method of claim 29, wherein said xanthan-containing fluid is present within a surface vessel or earthen mud or reserve pit.

31. The method of claim 29, wherein said step of combining includes the step of formulating said xanthan-containing fluid by combining said xanthanase enzyme complex with an aqueous fluid and an xanthan-containing polymer; and further comprising the steps of:

introducing said xanthan-containing fluid into a wellbore; and allowing said xanthanase enzyme complex to degrade said xanthan-containing polymer.

32. The method of claim 31, wherein said xanthan containing fluid is a well treatment fluid for at least one of hydraulic fracturing or gravel packing.

33. A method of treating a well penetrating a subterranean formation and having a well surface comprising the steps of:

formulating a gelable fluid by blending together an aqueous fluid, a xanthan polymer, a suitable cross linking agent to form a xanthan polymer gel, and an xanthanase enzyme complex produced by a soil bacterium bearing ATCC No. 55941;

introducing said xanthan polymer gel into said well; and allowing said xanthanase enzyme complex to degrade said xanthan in said polymer gel, whereby said fluid may be removed from said subterranean formation to said well surface.

34. The method of claim 33, wherein said gelable fluid is a blocking fluid.

35. The method of claim 33, wherein said gelable fluid is a fracturing fluid.

36. A method for producing an xanthanase enzyme complex, comprising the steps of:

culturing a bacterium bearing ATCC No. 55941 in a medium containing xanthan molecules under conditions suitable for the growth of said bacterium and for the production of xanthanase by said bacterium; and recovering said xanthanase from said medium.

37. An isolated and biologically pure microbial culture obtained from the bacterium bearing ATCC No. 55941.

38. An xanthanase contained in, or produced from, a solution comprising a culture of the bacterium bearing ATCC No. 55941.

* * * * *